United States Patent [19]

Shannon

[11] Patent Number: 5,097,029

[45] Date of Patent: Mar. 17, 1992

[54] PROCESS FOR PREPARING 2,3-DIHYDRO-1,3-DIALKYL-2,3-DIALKYL PERIMIDINES AND N,N'-DIALKYL-1,8-NAPHTHALENE DIAMINES

[75] Inventor: Paul J. Shannon, Exton, Pa.

[73] Assignee: Hercules Incorporated, Wilmington, Del.

[21] Appl. No.: 562,983

[22] Filed: Aug. 6, 1990

Related U.S. Application Data

[62] Division of Ser. No. 375,166, Jul. 3, 1989, Pat. No.

[51] Int. Cl.$^5$ .................. C07D 239/70; C07C 209/62
[52] U.S. Cl. .................. 544/249; 534/577; 534/754; 534/762; 564/413
[58] Field of Search .......... 544/249; 564/413

[56] References Cited

U.S. PATENT DOCUMENTS

| | | | |
|---|---|---|---|
| 2,850,532 | 9/1958 | Simon | 564/413 X |
| 3,185,538 | 5/1965 | Voltz et al. | 544/249 X |
| 4,122,027 | 10/1978 | Cole et al. | 252/299 |
| 4,128,497 | 12/1978 | Cole et al. | 252/299 |
| 4,179,395 | 12/1979 | Cole et al. | 252/299 |
| 4,224,071 | 9/1980 | Buell | 544/249 X |
| 4,319,046 | 3/1982 | Vacek | 564/413 |
| 4,401,369 | 8/1983 | Jones et al. | 350/349 |
| 4,565,424 | 1/1986 | Huffman et al. | 350/349 |
| 4,599,413 | 7/1986 | Moulton et al. | 544/249 X |
| 4,667,020 | 5/1987 | Etzbach et al. | 534/577 |

FOREIGN PATENT DOCUMENTS

2155544 5/1973 Fed. Rep. of Germany ...... 544/249
1318587 6/1987 U.S.S.R. ............................ 564/413

OTHER PUBLICATIONS

Alder et al., J. Chem. Soc. (London), vol. of 1981, pp. 2840 to 2847.
Gleiter et al., J. Org. Chem., vol. 51, pp. 370 to 380 (1986).
Ivashchenko et al., "Dyes in Liquid Crystals", Mol. Cryst. Liq. Cryst., vol. 150A, pp. 1 to 168 (1987).
Jeffreys, Chemical Abstracts, vol. 50, #78096 to 7810c (1956).
Pozharskii et al., Zh. Org. Kim., vol. 16, pp. 1890–1901 (1980).
Sokolov et al., Chemistry of Heterocyclic Compounds, vol. 11, pp. 782–784 (1975).

*Primary Examiner*—Mary C. Lee
*Assistant Examiner*—Fiona T. Powers
*Attorney, Agent, or Firm*—Mark D. Kuller

[57] ABSTRACT

Processes for preparing 2,3-dihydro-1,3-dialkyl-2,2-dialkyl perimidines and N,N'-dialkyl-1,8-naphthalene diamines are disclosed. The 2,3-dihydro-1,3-dialkyl-2,2-dialkyl perimidines are prepared by alkylating 2,3-dihydro-2,2-dialkyl perimidines with an alkylating agent in a water miscible organic solvent at room temperature to 80° C. in the presence of water and an inorganic base. N,N'-dialkyl-1,8-naphthalene diamines are prepared by hydrolyzing the 2,3-dihydro-1,3-dialkyl-2,2-dialkyl perimidines with strong aqueous acid in an aqueous organic solvent and removing a ketone by-product and the aqueous organic solvent by codistillation.

10 Claims, 4 Drawing Sheets

New route to N,N'-dialkyl-1,8-naphthalene diamines, with subsequent condensation to N,N'-dialkyl-2,3-dihydro-2,2-dialkyl or 2-alkyl perimidine.

R, R' = alkyl or H
R$_3$-X = C$_1$-C$_{20}$ alkyl halide (iodide or bromide), tosylate or mesylate
R$_3$ = C$_1$-C$_{20}$ alkyl
R$_4$, R$_5$ = H, C$_1$-C$_{20}$ alkyl, or form a cycloaliphatic ring

Drawings

$R_1$, $R_2$ = alkyl or H

R1, R2 = alkyl or H

DMF = dimethylformamide

R, R' = alkyl or H
$R_3$-X = $C_1$-$C_{20}$ alkyl halide (iodide or bromide), tosylate or mesylate
$R_3$ = $C_1$-$C_{20}$ alkyl
$R_4$, $R_5$ = H, $C_1$-$C_{20}$ alkyl, or form a cycloaliphatic ring

PROCESS FOR PREPARING 2,3-DIHYDRO-1,3-DIALKYL-2,3-DIALKYL PERIMIDINES AND N,N'-DIALKYL-1,8-NAPHTHALENE DIAMINES

This application is a division of application Ser. No. 07/375.166, filed July 3, 1989, now abandoned.

This invention is directed to novel arylazo and poly(arylazo) dyes having at least one 2,3-dihydro-1,3-dialkyl perimidine substituent, and syntheses of the same.

BACKGROUND OF THE INVENTION

The use of dichroic dyes in solution with various liquid crystal materials, e.g., nematic liquid crystals and blends thereof, and use of these so-called "guest-host" mixtures in liquid crystal devices, e.g., liquid crystal displays, are well known. In liquid crystal displays, the host liquid crystal material has its orientation controlled by the application of electric fields and in turn interacts with the guest dichroic dye to induce a cooperative conforming alignment. The dichroic dyes manifest low or high absorbance of incident light depending upon their molecular orientation with respect to the light wave vector. Generally, when an electric field is applied to the display, the area between the electrodes appears clear, i.e., all the dyes exhibit minimum absorption, and in the absence of an electric field the display appears dye colored, i.e., the dyes are in a high absorbing state.

Dyes suitable for such guest-host mixtures must have high order parameters and proper solubility in the host liquid crystal material, and the guest-host mixtures should provide good viewing characteristics (e.g., high contrast), high extinction, and chemical and photochemical stability.

Several patents describe dichroic azo dyes that have N,N'-unsubstituted dihydroperimidines as end group moieties. For example, Huffman et al, in U.S. Pat. No. 4,565,424, describe poly(arylazo) dyes containing a 2,3-dihydro-2,2-disubstituted perimidine moiety; Etzbach et al, in U.S. Pat. No. 4,667,020, describe diazo dyes containing a 2,3-dihydro-2,2-disubstituted perimidine moiety; and Cole, Jr. et al, in U.S. Pat. No. 4,122,027, describe a pentaazo dye containing a 2,3-dihydro-2,2-disubstituted perimidine moiety. In each of these cases the nitrogen atoms at the 1 and 3 positions of the dihydroperimidine are bound to a hydrogen atom.

Azo dyes containing dihydroperimidine moieties unsubstituted at the nitrogen positions exhibit relatively low solubility characteristics in nematic hosts. The N—H bonds in the dyes result in relatively high crystalline melting points and thus solubility is reduced. The inventor has studied the solubility of such dyes and discovered that azo dyes having N,N'-disubstituted-2,3-dihydro perimidine end groups, particularly those with alkyl substitution at the 2-position, are more soluble than the same dyes having N—H bonds. Guest-host mixtures prepared with such dyes have excellent properties, most notably improved contrast.

Azo dyes having N,N'-disubstituted-2,3-dihydro perimidine end groups, however, require for their formation 2,3-dihydro-1,3-dialkyl perimidines. Prior to this invention, this class of compounds had not been readily accessible, and thus, the polyazo dyes having end groups derived therefrom had not been prepared.

Figure 1:
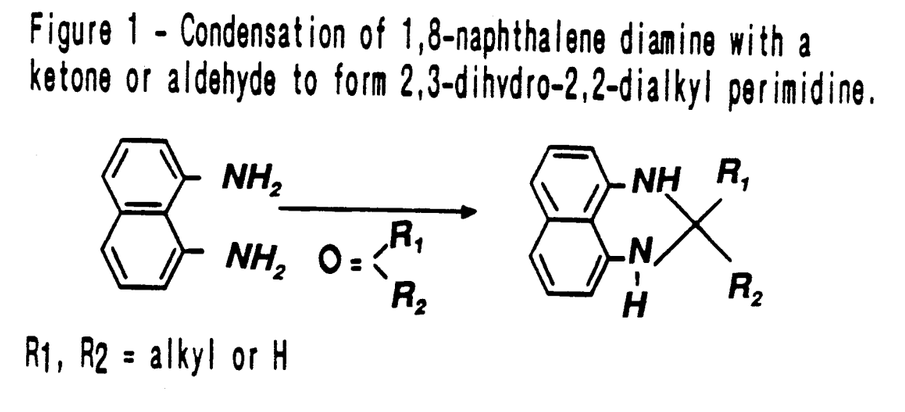
Figure 1 - Condensation of 1,8-naphthalene diamine with a ketone or aldehyde to form 2,3-dihydro-2,2-dialkyl perimidine.

2,3-dihydro-2,2-dialkyl perimidines cited in the Huffman, Etzbach and Cole patents are readily accessible by condensation of 1,8-naphthalene diamine with a ketone or aldehyde as outlined in FIG. 1. Up to now, however, N,N'-dialkyl-1,8-naphthalene diamines have not been readily accessible.

Figure 2:
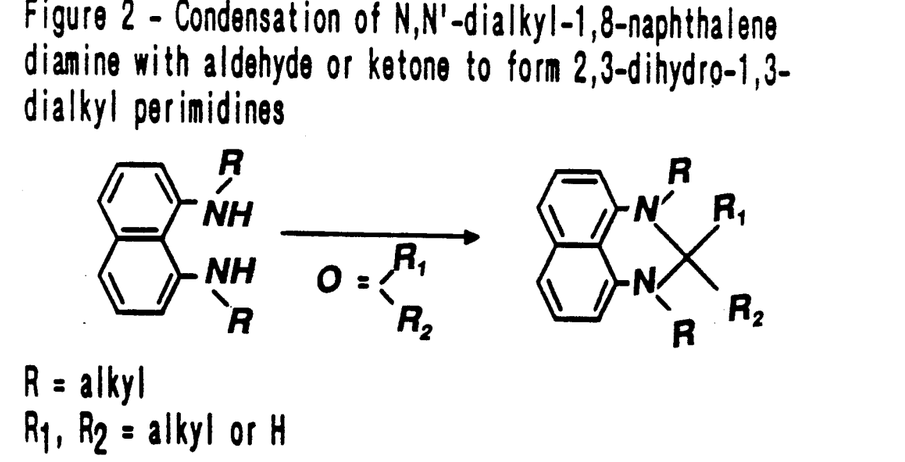
Figure 2 - Condensation of N,N'-dialkyl-1,8-naphthalene diamine with aldehyde or ketone to form 2,3-dihydro-1,3-dialkyl perimidines R = alkyl
$R_1$, $R_2$ = alkyl or H Figure 3 – Reduction of diacetamide of 1,8-naphthalene diamine to N,N'-diethyl-1,8-naphthalene diamine Figure 4 – New reductive methylation of 2,3-dihydro-2,2-dialkyl perimidine.
Figure 3:
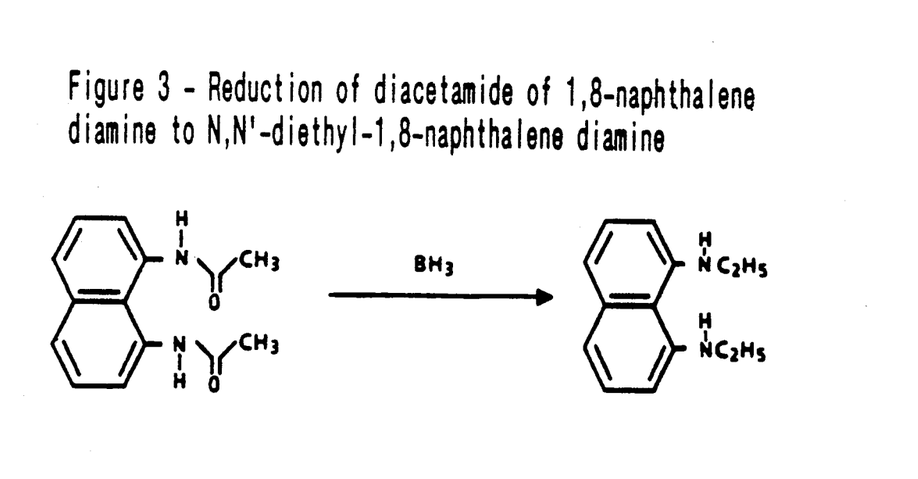
Figure 5:
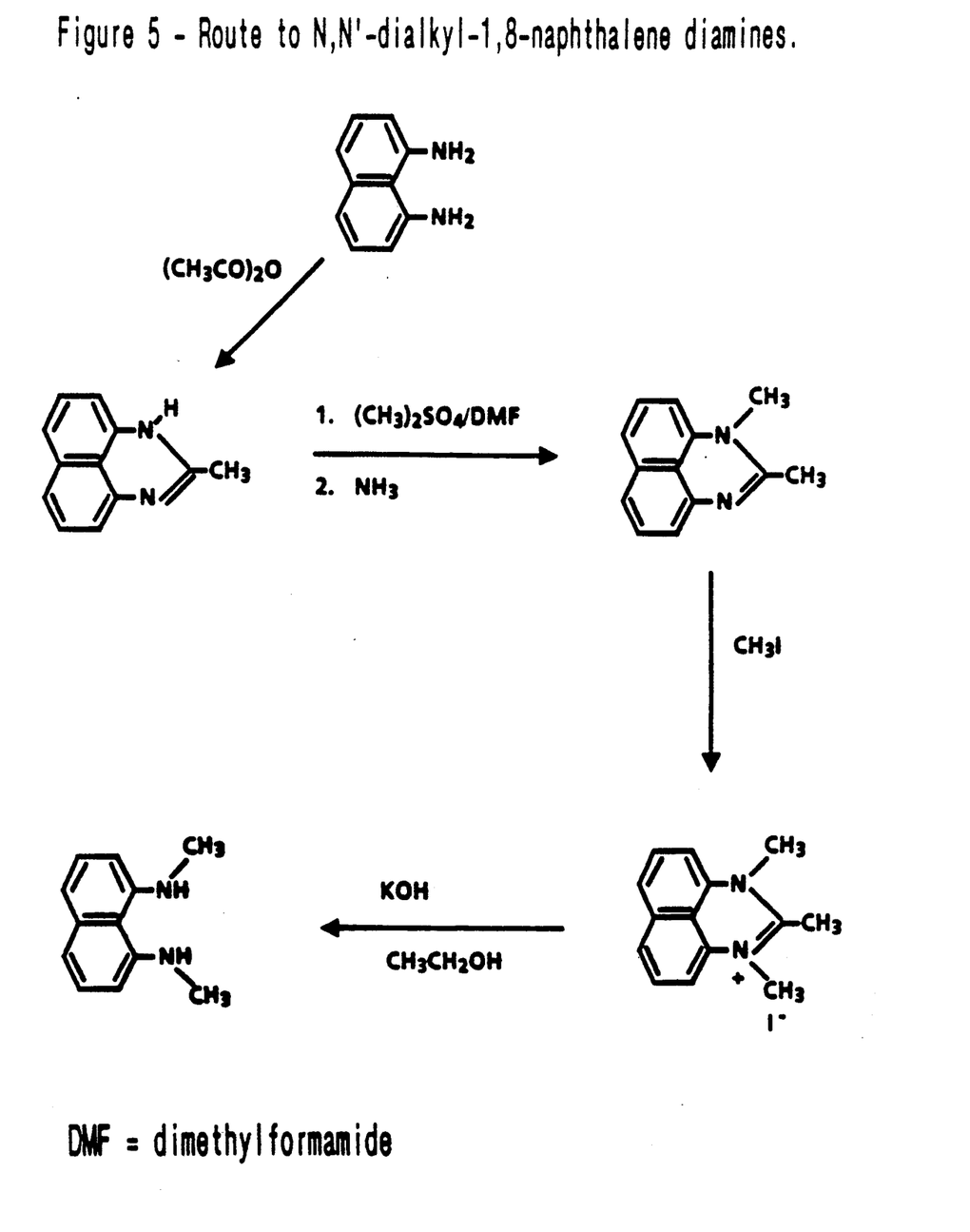
Figure 5 - Route to N,N'-dialkyl-1,8-naphthalene diamines.

Two routes are known to prepare 2,3-dihydro-1,3-alkyl perimidines. As a preliminary step, N,N'-dialkyl-1,8-naphthalene diamine is synthesized. One route for synthesizing N,N'-dialkyl-1,8-naphthalene diamines, outlined in FIG. 5 (A. F. Pozharskii et al, Zh. Org. Khim., 16, (10) 2216 (1980) and Chemistry of Heterocyclic Compounds, Plenum Press, New York p 782 (1975) (Translated from Khim. Geterot. Soed., No. 6, 849 (1973))), requires condensation of 1,8-naphthalene diamine with acetic anhydride to give 2-methyl perimidine. Alkylation of the perimidine with dimethyl sulfate and basification with ammonia gives 1,2-dimethyl perimidine; alkylation with methyl iodide gives the methiodide salt; and hydrolysis gives the desired N,N'-dimethyl-1,8-naphthalene diamine. A second route, outlined in FIG. 3, requires the reduction of the diacetamide of 1,8-naphthalene diamine (R. W. Alder, et al, J. Chem. Soc., Pt. 1, 2840 (1981)). 2,3-Dihydro-1,3-dialkyl-2,2-dialkyl perimidines can then be made by condensation of N,N'-dialkyl-1,8-naphthalene diamines with aldehydes or ketones as outlined in FIG. 2. Both methods of forming N,N'-dialkyl-1,8-naphthalene diamines have limitations and have not been found to be applicable to the synthesis of a variety of N,N'-dialkyl-1,8-naphthalene diamines.

The inventor has developed a new route to N,N'-dialkyl-1,8-naphthalene diamines, described below, making it possible to readily, easily and economically prepare such compounds in high yields and to prepare dichroic dyes having end groups derived from such compounds.

SUMMARY OF THE INVENTION

Accordingly, this invention is directed to arylazo and poly(arylazo) dichroic dyes having at least one 2,3-dihydro-1,3-dialkyl perimidine substituent. In addition, this invention is directed to processes for preparing N,N'-dialkyl-1,8-napahalene diamine and 2,3-dihydro-1,3-dialkyl-2,2-dialkyl permidine intermediates useful for preparing such polyazo dichroic dyes using novel syntheses.

DETAILED DESCRIPTION OF THE INVENTION

Preferred are arylazo or poly(arylazo) dichroic dyes having at least one 2,3-dihydro-1,3-dialkyl perimidine substituent have the general formula:

wherein n is an integer of 0 through 4, $R_1$ and $R_2$, which may be the same or different in different moieties, are selected from hydrogen, —$CH_3$, —$OCH_3$, —CN, —$NO_2$, —OH, Cl, Br and F; Y is a 2,3-dihydro-1,3-dialkyl perimidine:

(A)

wherein $R_3$ is selected from the group consisting of $C_1$-$C_{10}$ alkyl groups, $R_4$ and $R_5$, which can be the same or different, are selected from the group consisting of H and $C_1$-$C_{20}$ alkyl groups or form a cycloaliphatic ring;

(B)

wherein Z is $R_8O-$, $R_9CO_2-$, $-NO_2$, $-CN$, Cl, Br, F and $R_8$ and $R_9$, which may be the same or different, are selected from the group consisting of $C_1$-$C_{10}$ alkyl groups. $R_{10}$ and $R_{11}$ are hydrogen or $C_1$-$C_{20}$ alkyl groups. $R_6$ and $R_7$, which may be the same or different, are hydrogen, $-CH_3$, $-OCH_3$, $-CN$, $-NO_2$, $-OH$, Cl, Br or F, (C)

wherein $R_{10}$ and $R_{11}$ are as described above, or (D)

wherein $R_{12}$ is selected from the group consisting of H and $C_1$-$C_{10}$ alkyl groups, $R_{13}$ and $R_{14}$, which can be the same or different, are selected from the group consisting of H and $C_1$-$C_{20}$ alkyl groups or form a cycloaliphatic ring.

Cycloaliphatic rings formed by $R_4$ and $R_5$, or $R_{13}$ and $R_{14}$ typically contain 4 to 8 carbon atoms.

The dyes of this invention may be synthesized through a number of routes.

N,N'-dialkyl-1,8-naphthalene diamines may be synthesized as disclosed in the literature (Pozharskii et al—FIG. 5 and Alder et al—FIG. 3), described above.

Figure 6:
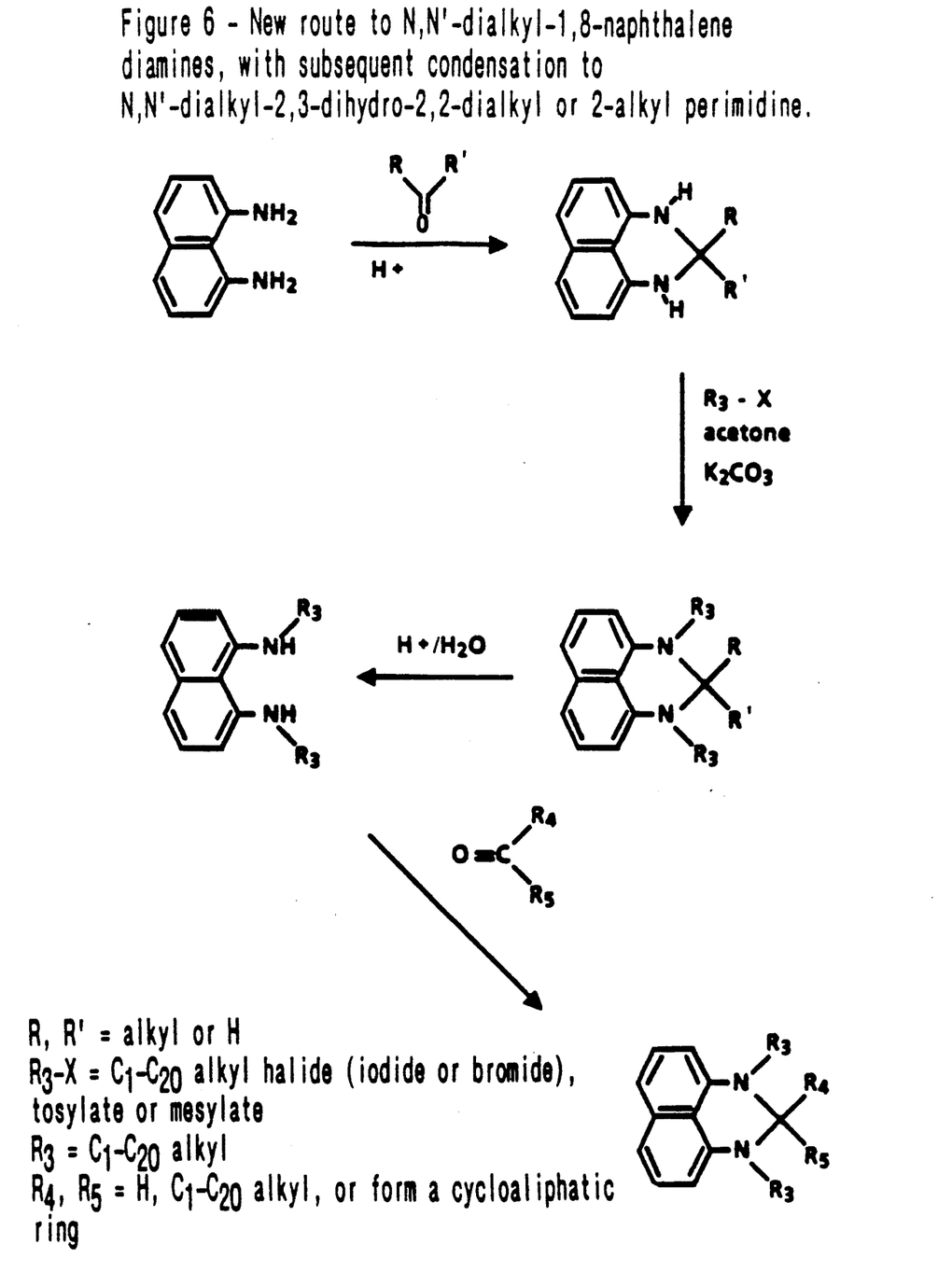
Figure 6 - New route to N,N'-dialkyl-1,8-naphthalene diamines, with subsequent condensation to N,N'-dialkyl-2,3-dihydro-2,2-dialkyl or 2-alkyl perimidine.

N,N'-dialkyl-1,8-naphthalene diamines are preferably synthesized according to a new route outlined in FIG. 6. That is, condensation (preferably at room temperature) of 1,8-naphthalene diamine with a ketone or aldehyde (e.g., 3-methyl-2-butanone, acetone, methyl ethyl ketone, cyclopentanone, cyclohexanone, etc., preferably 3-methyl-2-butanone or acetone) gives a 2,3-dihydro-2,2-dialkyl perimidine. This material is alkylated (room temperature $-80°$ C.) at each nitrogen atom with an alkyl halide (preferably bromide or iodide), alkyl tosylate or alkyl mesylate alkylating agent (e.g., methyl iodide, butyl iodide, methyl bromide, octyl bromide, methyl tosylate, octyl tosylate, methyl mesylate, decyl mesylate, etc.) in a water miscible organic solvent (e.g., acetone, methyl ethyl ketone, tetrahydrofuran or dimethylformamide, etc., with acetone and methyl ethyl ketone being preferred) in the presence of water and an inorganic base (e.g., potassium carbonate, sodium carbonate, sodium hydroxide, potassium hydroxide, etc., preferably potassium carbonate) in a one pot process.

The steric hindrance about the nitrogen atoms of the 2,3-dihydro-2,2-dialkyl perimidines controls the selectivity of the alkylation reaction. With methyl iodide, methyl tosylate, methyl mesylate, methyl bromide and the like high steric hindrance and low temperatures (e.g., room temperature) are preferred. With higher homologs, such as n-butyl iodide, octyl bromide, etc., less steric hindrance and higher temperatures (e.g., $60°$-$80°$ C.) are preferred.

Hydrolysis ($60°$-$100°$ C.) of the 2,3-dihydro-1,3-dialkyl-2,2-dialkyl perimidine in aqueous acid (e.g., hydrochloric acid, sulfuric acid, para-toluene sulfonic acid, etc., preferably hydrochloric acid) and an aqueous organic solvent (preferably water-miscible, non-ketone solvent (e.g., tetrahydrofuran, ethanol, methanol, etc., preferably tetrahydrofuran) in water) provides N,N'-dialkyl-1,8-naphthalene diamine. The hydrolysis requires the removal of the ketone by-product as it is formed in the reaction. The aqueous organic solvent is distilled during the reaction to drive over the ketone by-product as it is formed. Table 1 lists various N,N'-dialkyl-1,8-naphthalene diamines prepared by the route outlined in FIG. 6.

2,3-Dihydro perimidines derived from acetone are very resistant to hydrolysis. All the solvent and much of the aqueous acid must be distilled to drive the hydrolysis to completion. 2,3-Dihydro perimidines derived from 3-methyl-2-butanone are hydrolyzed very readily. The reaction is usually complete when all the organic solvent has been distilled.

The N,N'-dialkyl-1,8-naphthalene diamines are easily purified by recrystallization. They can then be used to prepare a wide variety 2-substituted or 2,2-disubstituted 2,3-dihydro-1,3-dialkyl-perimidines by condensation with aldehydes or ketones as outlined in FIG. 2. Condensations are usually carried out at room temperature in the presence of a catalytic amount of p-toluene sulfonic acid. The aldehyde or ketone can be used as solvent, as in the case of the acetone adduct, or a slight excess of the aldehyde or ketone can be used in an inert solvent such as tetrahydrofuran or ethyl acetate. Table 2 lists various 2,3-dihydro-1,3-dialkyl perimidines prepared by condensation of aldehydes or ketones with N,N'-dialkyl-1,8-naphthalene diamines.

Figure 4:
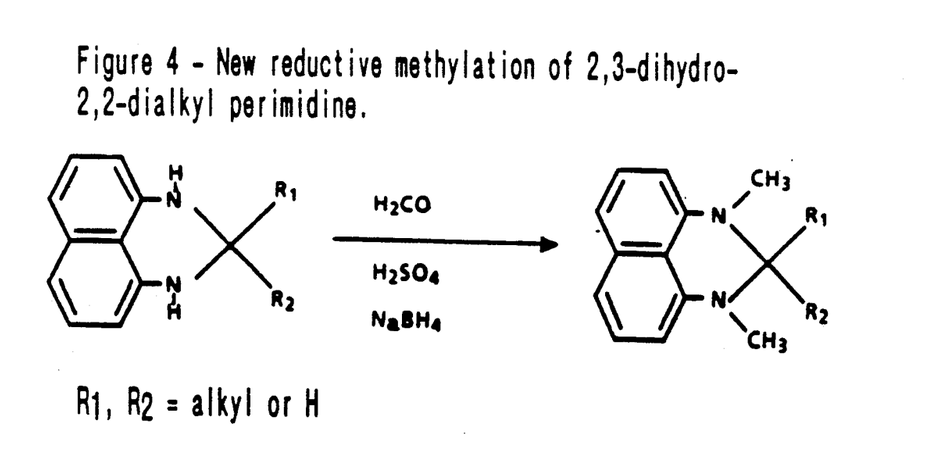

An alternative, novel but less preferred, method for making 2,3-dihydro-1,3-dialkyl perimidines is reductive methylation of 2,3-dihydro perimidines with sodium borohydride and formaldehyde in aqueous sulfuric acid as outlined in FIG. 4. This process works well on a small scale when the 2-alkyl substituents of the perimidines are short carbon chains such as gem dimethyl or propyl. If longer alkyl groups are present at the 2-position, significant amounts of dimeric materials are formed.

The poly(arylazo) moieties, moieties (B) and (C), and their preparation are well-known as shown, e.g., by Huffman et al in U.S. Pat. No. 4,565,424, Jones et al, in U.S. Pat. No. 4,401,369, Cole, Jr. et al, in U.S. Pat. Nos. 4,122,027, 4,128,497 and 4,179,395, Etzbach et al, in U.S. Pat. No. 4,667,020, and Ivashchenko et al, "Dyes in Liquid Crystals", Mol. Cryst. Liq. Cryst., Vol. 150 A, pp. 1-168 (1987). Moiety (D) is prepared according to the methods of preparing moiety (A) or other well-known processes, including those shown in the aforementioned patents.

A preferred synthetic scheme for preparing the dichroic dyes of this invention involves direct diazotization of the appropriate 4-substituted aniline in strong mineral acid, followed by coupling the resultant diazo compound to the appropriate substituted aniline. Diazotization and coupling are repeated as desired and the intermediate products are recovered from a buffered aqueous solution as the free base and purified by recrystallization. The free base is subsequently diazotized and coupled with the desired substituted 2,3-dihydro perimidine in acid. The resultant dichroic dye is recovered from the neutralized solution by filtration and is purified by recrystallization or chromatography. Exemplary dyes prepared by these methods are shown in Tables 3, 4 and 5.

The dichroic dyes of this invention exhibit deep blue to orange color and have absorption maxima at wavelengths in the range of about 450 to about 700 nanometers. The peak absorption value (lambda max) shifts to higher wavelengths and the extinction coefficient increases with an increase in the length of the alkyl group at the number two carbon atom ($R_4$ and $R_5$ of the formula (I)) and the number one and three nitrogen atoms ($R_3$ of formula (I)). Similarly, the peak absorption value shifts to higher wavelengths when an alkyl group is substituted for a hydrogen atom at one or more of these positions.

The dyes of this invention are stable towards UV light and heat.

Although the dyes of this invention may be used in any application where similar dyes may be used, they are primarily intended for use in guest-host liquid crystal mixtures comprising at least one liquid crystal and at least one dichroic dye soluble in the liquid crystal. Herein, the term "liquid crystal" is used to refer to molecules with anisotropic geometry, such as rod-shaped or disc-shaped, that exhibit stable states intermediate between liquid and solid, and which have low molecular weights. The liquid crystal medium of this invention may contain any such liquid crystal compound useful in liquid crystal devices, e.g., liquid crystal displays, or a mixture of such liquid crystal compounds. Useful are thermotropic liquid crystals which exhibit nematic and smectic (including ferroelectric) phases.

Nematic phases include conventional uniaxial nematics, twisted nematic, and cholesteric mesophases. The nematic liquid crystals can have either positive or negative dielectric anisotropy. As used herein the term "positive" or "negative" refers to the net dielectric anisotropy of a mixture comprising liquid crystals.

Readily available positive nematic liquid crystal materials which are suitable for the practice of this invention include:
4-cyano-4'-alkylbiphenyls,
4-cyano-4'-alkyloxybiphenyls,
4-alkyl-(4'-cyanophenyl)cyclohexanes,
4-alkyl-(4'-cyanobiphenyl)cyclohexanes,
4-cyanophenyl-4'-alkylbenzoates,
4-cyanophenyl-4'-alkyloxybenzoates,
4-alkyloxyphenyl-4'-cyanobenzoates,
4-alkylphenyl-4'-cyanobenzoates,
1-(4'-alkylphenyl)-4-alkylpyrimidines,
1-(4'-alkylphenyl)-4-cyanopyrimidines,
1-(4'-alkyloxyphenyl)-4-cyanopyrimidines, and
1-(4-cyanophenyl)-4-alkylpyrimidines.

Specific examples of compounds within these families are:
4-cyano-4'-pentylbiphenyl,
4-cyano-4'-hexyloxybiphenyl,
trans-4-pentyl-(4'-cyanophenyl)cyclohexane,
trans-4-hexyl-(4'-cyanobiphenyl)cyclohexane,
4-cyanophenyl-4'-propylbenzoate,
4-pentyloxyphenyl-4'-cyanobenzoate,
4-hexylphenyl-4'-cyanobenzoate,
1-(4'-pentylphenyl)-4-butylpyrimidine,
1-(4'-butyloxyphenyl)-4-cyanopyrimidine,
1-(4-cyanophenyl)-4-alkylpyrimidine,
4-n-hexylbenzylidene-4'-aminobenzonitrile and
4-cyanobenzylidene-4'-octyloxyaniline.

Eutectic mixtures and combinations of all the above are also useful. Illustrative are eutectic mixtures of 4'-alkyl-4-cyanobiphenyls with either 4'-alkyloxy-4-cyanobiphenyls wherein the 4' substituents have 3 to 8 carbons or terphenyl liquid crystals with 4-alkyl or alkyloxy substituents containing 3 to 8 carbon atoms. Representative are the commercially available E7 mixture from BDH, Ltd., Poole, England; ROTN 404, a eutectic mixture of biphenyl pyrimidine liquid crystals from Hoffman La Roche, Nutley, N.J.; PCH 1132, a mixture comprising the 4-alkyl-(4'-cyanobiphenyl)cyclohexanes and 4-alkyl-(4'-cyanophenyl)cyclohexanes from EM Industries, Hawthorne, N.Y.; and ZLI 1982, also available from EM Industries.

Representative of nematic liquid crystals having negative dielectric anisotropy that would be useful for this invention include:
4-alkyloxy-4'-alkyloxyazoxybenzenes,
4-alkyl-4'-alkyloxyazoxybenzenes,
4-alkyl-4'-acyloxyazoxybenzenes,
4-alkyl-4'-alkylazoxybenzenes and
4-alkyl-2-cyanophenyl-4'-alkylbiphenyl-1-carboxylates.

Specific examples include:
p-azoxyanisole,
4-butyl-4'-hexyloxyazoxybenzene,
4-butyl-4'-acetoxyazoxybenzene,
4,4'-bis(hexyl)azoxybenzene, and
4-pentyl-2-cyanophenyl-4'-heptylbiphenyl-1-carboxylate.

Commercially available are Licristal S1014 from EM Industries, Hawthorne, N.Y.; and EN-18 from Chisso Corp, Yokohama, Japan.

Smectic A liquid crystals useful in this invention can be of either positive or negative dielectric anisotropy. Smectic A liquid crystals of positive anisotropy include:
4-alkyl-4'-cyanobiphenyls and 4-cyano-4'-alkylbenzylideneanilines, as well as mixtures of
4-alkyl-4"-cyano-p-terphenyls and
4-alkyl-4"-cyanobiphenyls. Also useful are smectic A mixtures derived from electron accepting and electron donating mesogenic cores, for example 4'-alkylphenyl 4-alkylbenzoates and 4'-cyanophenyl-4"-alkyloxybenxoyloxybenzoates. Specific examples of compounds useful as smectic A liquid crystals with positive dielectric anisotropy are:
4-cyano-4'-octylbenzylideneaniline,
4-decyl-4'-cyanobiphenyl,
4-dodecyl-4"-cyano-p-terphenyl,
4'-heptylphenyl-4-butylbenzoate and
4'-cyanophenyl-4"-octyloxybenzoyloxybenzoate.
Eutectic mixtures and combinations of all the above smectic A materials are useful. Representative eutectic mixtures and combinations of smectic A liquid crystals are the commercially available materials S1, S2, S3, S4, S5, S6 and S7, from EM Industries, Hawthorne, N.Y.

Representatives of smectic A liquid crystals of negative dielectric anisotropy that are useful in this invention are
4-alkylphenyl-4-alkyloxy-3-cyanobenzoates,
4-alkyloxyphenyl-4-alkyloxy-3-cyanobenzoates and
4"-alkyloxyphenyl-4'-alkyloxybenzoyloxy-3-cyanobenzoates.
Specific examples include:
4'-octylphenyl-4-decyloxy-3-cyanobenzoate,
4'-decyloxyphenyl-4-octyloxy-3-cyanobenzoate and
4'-heptyloxyphenyl-4'-decyloxybenzoyl-3-cyanobenzoate.
Eutectic mixtures of these may also be used.

Representative chiral smectic C liquid crystals useful in the practice of this invention include:
4'-alkyloxyphenyl-4-alkyloxybenzoates,
4'-alkyloxybiphenyl-4-alkyloxybenzoates,
4-alkyloxyphenyl-4-alkyloxybiphenylcarboxylates and terpenol esters of 4'-n-alkyloxybiphenyl-4-carboxylates. Specific examples are:
4(4-methylhexyloxy)phenyl-4-decyloxybenzoate,
4-heptyloxyphenyl-4(4-methylhexyloxy)benzoate,
4'-octyloxybiphenyl-4(2-methylbutyloxy)benzoate,
4-nonyloxyphenyl-4'-(2-methylbutyloxy)biphenyl-4-carboxylate, and
menthyl 4'-n-octyloxybiphenyl-4-carboxylate.
Commercially available mixtures of chiral smectic C liquid crystals include the CS 1000 series offered by Chisso Corp., Yokohama, Japan; ZLI 4139, available from EM Industries, Hawthorne, N.Y.; and the eutectic mixtures of laterally fluorinated esters developed by BDH, LTD., and available through EM Industries as the SCE series of eutectic mixtures SCE3 through SCE12. Single component chiral smectic C materials based on 4'-alkyloxyphenyl-4-alkyloxybenzoates, W7, W37, W81, and W82 are available from Displaytech, Inc., Boulder, Colo.

Preferred for use in guest-host mixtures for liquid crystal displays are dyes having substituents (B) or (D), with group (D) being most preferred. When substituent (B) is present, preferably $R_3$ is $CH_3$, $R_4$ is H, $R_5$ is $C_3$-$C_{12}$ alkyl, Z is $R_8O-$ wherein $R_8$ is $C_1$-$C_{10}$ alkyl, and $R_6$ and $R_7$ are H. When substituent (D) is present, $R_3$ and $R_{12}$ are preferably $C_1$-$C_8$ alkyl, $R_4$ and $R_{13}$ are preferably H, and $R_5$ and $R_{15}$ are preferably $C_3$-$C_{12}$ alkyl. Most preferably with nematic liquid crystals the dyes are tetraazo (n=3) wherein on the first aromatic unit $R_1$ and $R_2$ are H, on the second aromatic unit $R_1$ is H and $R_2$ is $CH_3$, and on the third aromatic unit $R_1$ is $CH_3$ and $R_2$ is $OCH_3$. Also preferred with nematic liquid crystals are similar pentaazo dyes. With smectic liquid crystals, similar di- and tri-azo dyes are preferred, with the di-azo dyes being the most preferred of these two.

The dyes of this invention are quite soluble in the aforementioned liquid crystals. Solubility in host liquid crystals initially increases with increasing length of an alkyl chain at the number two carbon position, and then falls off with longer homologs (e.g., between $C_3$ and $C_8$ in a nematic host). Longer alkyl substituents on the nitrogen sites dramatically improve the solubility of the dye, particularly in nematic hosts.

The dyes of this invention have relatively high values of the optical order parameter S in nematic hosts. This parameter is a measure of the efficiency with which the dye is oriented by the liquid crystal material and is directly related to the contrast observed when viewing a liquid crystal device. In general, dyes having high optical order parameters produce devices having high contrasts. Optical order parameter is measured using the following formula:

$$S = \frac{D-1}{D+2}$$

wherein $D = A_0/A_1$, $A_0$ is the absorbance in the absence of an electric field and $A_1$ is the absorbance in the presence of an electric field. S is a value less than 1 and is preferably very close to 1. In nematic hosts, the dyes of this invention have values of S greater than about 0.72, insuring optical contrast ratios on the order of at least 10:1. Preferred dyes have, in nematic hosts, S values greater than about 0.78, and most preferably about 0.8 or higher.

One notable feature of this invention is that it is possible to produce tri-, tetra- and penta-azo blue dyes (absorption maxima at wavelengths in the range of about 600 to about 700 nanometers) having high solubility and order parameter in nematic liquid crystal hosts.

The dyes of this invention have relatively high extinction coefficients. The molar extinction coefficient is a measurement of the extent to which the dye absorbs light at any particular molar concentration. Therefore, the dyes of this invention, with higher molar extinction coefficients provide displays with better brightness characteristics at any particular molar concentration of dichoric dye.

Guest-host systems made with the dyes of this invention are useful in liquid crystal display devices having conventional configurations (e.g., two, three or more substrate structures) and may include one or more polarizers, lighting means, reflective or transflective layers, alignment layers, elastomeric connectors and circuit boards as conventionally used in the art. Other conventional materials such as conducting ionic dopants, chiral dopants, photostabilizers and viscosity modifiers, etc., may be used.

In guest-host mixtures, the dyes of this invention may be used in combination with other dyes. Dyes useful in these mixtures include dichroic azo, diazo, triazo, tetraazo, pentaazo, anthraquinone, mericyanine, methine, 2-phenylazothiazole, 2-phenylazobenzthiazole, 4,4'-bis(arylazo)stilbenes, perlyne and 4,8-diamino-1,5-naphthaquinone dyes, and other dyes that exhibit dichroic absorption bands.

Such guest-host systems are useful for other liquid crystal devices. e.g., all-optical light modulators, erasable read/write optical data storage media. etc. The dyes themselves are also useful in textiles, printing, color filters, polarizers, paints, electro-optical modulators, etc.

This invention is demonstrated in the following examples, which are illustrative and not intended to be limiting, wherein all percentages, are by weight.

The liquid crystal materials used in the examples are ZLI 1982, a nematic mixture with an isotropic transition of 90° C. (EM Industries, Hawthorne N.Y.), ZLI 2452, a nematic mixture with an isotropic transition of 110° C. (EM Industries), and CS 1018, a chiral smectic C (ferroelectric) mixture (Chisso Corp., Yokohama, Japan). All of the other starting materials were purchased from Aldrich Chemical Co., Inc., Milwaukee, Wis., and were used without purification unless otherwise indicated.

EXAMPLE 1

This example illustrates the preparation of a N,N'-dimethyl-1,8-naphthalene diamine shown in Table 1 using the procedure of FIG. 6.

1,8-Naphthalene diamine was distilled on a Kugelrohr distillation apparatus (Aldrich Chemical Co.) at 140°-160° C. (0.1 mm Hg) to give a pink solid. Then, a mixture of the distilled 1,8-naphthalene diamine (21.8 g, 0.138 mol, Molecular Weight 158), p-toluene sulfonic acid (0.75 g), and 3-methyl-2-butanone (24.6 g, 0.30 mol, molecular weight 82) was prepared, stirred at 50°-60° C. for 1 hour, and allowed to sit overnight at room temperature. The mixture was transferred to a 500 ml 3-neck flask. Water (30 ml), acetone (150 ml), potassium carbonate (84 g, 0.6 mol), and iodomethane (84 g, 0.60 mol) were added and the mixture mechanically stirred at 60°-70° C. for 2 hours, after which more iodomethane (21.0 g, 0.15 mol) was added. The reaction was monitored by thin layer chromatography (TLC) using hexane-ethyl acetate (5:1) as an eluting solvent. After 5.5 hours, the excess methyl iodide and some acetone (25 ml) were distilled and the mixture diluted with water (500 ml) and extracted with ether (2 times, 400 ml and 200 ml portions). The ether extracts were washed with brine and concentrated to a black solid. The solid was dissolved in distilled tetrahydrofuran (THF) (100 ml) and 2N HCl (in distilled water) (300 ml). TLC indicated that the hydrolysis reaction was complete. The mixture was cooled, basified to a pH greater than 11 with ammonium hydroxide (150 ml) and extracted with ether (400 ml and 200 ml portions). The extract was washed with brine, dried over potassium carbonate and concentrated to a solid. The solid was distilled (Kugelrohr, 98°-102° C., at 0.1 mm Hg) to give a beige solid (21.4 g). The solid was dissolved in hot ethyl acetate (40 ml) and diluted with hexane (160 ml). Cooling gave crystals of N,N'-dimethyl-1,8-naphthalene diamine (15.1 g, 59%): melting point (mp) 102°-104° C.; NMR (CDCl$_3$) 7.15(m, 4H), 7.5(d of d, 2H), 5.4(bs, 2H), 2.85(s, 6H); IR (KBr) 3360, 1595 cm$^{-1}$.

EXAMPLE 2

This example illustrates the synthesis of a N,N'-dibutyl-1,8-naphthalene diamine shown in Table 1 using the procedure of FIG. 6.

A mixture of distilled 1,8-naphthalene diamine (0.14 mol) (distilled as described in Example 1), 3-methyl-2-butanone (24.6 g, 0.28 mol) and p-toluene sulfonic acid (0.75 g) was prepared and stirred at room temperature for 1 hour, and, then, allowed to sit overnight. Acetone (150 ml), water (30 ml), potassium carbonate (84 g, 0.61 mol), and n-butyl iodide (110 g, 0.60 mol) were added to the mixture, the mixture was heated to 60°-70° C., and stirred at that temperature for 25 hours. Potassium carbonate (42.0 g, 0.305 mol) and n-butyl iodide (55 g, 0.30 mol) were added, the mixture was heated to 60°-70° C., and stirred at that temperature for 19 hours. The mixture was diluted with water (750 ml) and extracted with ether (600 ml and 300 ml portions). The extract was washed with brine, dried over potassium carbonate, and concentrated. The mixture was heated in a Kugelrohr apparatus to 60° C. at 0.1 mm Hg to remove 1-butanol. The remaining mixture, comprising the dialkylated, monoalkylated and nonalkylated product (by TLC analysis) was purified by column chromatography on silica (hexane-ethyl acetate, 20:1) to give predominately the desired dialkylated product (20.7 g). The material was dissolved in THF (100 ml) and 2N HCl (300 ml) and heated to distill THF (100 ml). The mixture was basified with ammonium hydroxide, and extracted with ether (400 ml and 200 ml portions). The extract was washed with brine, dried over potassium carbonate, and concentrated. The residue was distilled on a Kugelrohr apparatus up to 120° C. (0.1 mm Hg) to give a beige solid (12.8 g). Recrystallization from ethyl acetate-hexane (3:2) gave N,N'-dibutyl-1,8-naphthalene diamine as needles (5.4 g, 14%): mp 63°-64° C.; NMR (CDCl$_3$) 7.1(m, 4H), 6.4(m, 2H), 5.35(bs, 2H), 3.02(t, 4H), 1.8-1.3(m, 8H), 0.95(t, 6H),; IR (KBr) 3330, 1595 cm$^{-1}$.

EXAMPLE 3

This example illustrates the preparation of a N,N'-dioctyl-1,8-naphthalene diamine shown in Table 1 using the procedure of FIG. 6.

A mixture of distilled 1,8-naphthalene diamine (15.8 g, 0.10 mol) (distilled as described in Example 1), acetone (100 ml) and p-toluene sulfonic acid (0.50 g) was prepared and stirred at room temperature for 15 minutes. Potassium carbonate (55.0 g, 0.40 mol), water (20 ml) and n-octyl iodide (96 g, 0.40 mol) were added to the mixture, and the mixture heated to 65°-70° C. and stirred for 24 hours. Potassium carbonate (27.5 g, 0.20 mol) and n-octyl iodide (48 g, 0.20 mol) were added and the heating continued for another 24 hours. The mixture was diluted with water and extracted two times with 500 ml portions of ether. The ether extract was washed with water and brine, dried over potassium carbonate, and concentrated. The mixture was heated in a Kugelrohr apparatus to 80° C. at 0.1 mm Hg to remove excess n-octyl iodide. The remaining material in the pot was purified by chromatography to give 14.5 g of an oil. The oil was dissolved in THF (200 ml) and 2N hydrochloric acid (200 ml) and heated to distill all the THF and 100 ml of the aqueous acid. The mixture was basified with ammonium hydroxide, and extracted with ether (500 ml and 300 ml portions). The extract was washed with brine, dried over potassium, and concentrated. The residue was purified by chromatography with hexane-ether 20:1 to give a tinted orange solid (2.0 g): mp 42°-43° C.; NMR (CDCl$_3$) 7.1 (m, 4H), 6.45(m, 2H), 5.42(bs, 2H), 3.05(t, 4H), 1.8-1.3(m, 24H), 0.95(t, 6H); IR (CHCl$_3$) 3330, 1598 cm$^{-1}$.

TABLE 1

N,N'-Dialkyl-1,8-Naphthalene Diamines of Examples 1-3

| Example No. | $R_3$ | Melting Point (°C.) |
|---|---|---|
| 1 | $CH_3$ | 101.5-103.5 |
| 2 | $C_4H_9$ | 63-64 |
| 3 | $C_8H_{17}$ | 42-43 |

EXAMPLE 4

This example illustrates the preparation of 2,3-dihydro-2,2-dimethyl perimidine (shown in Table 2), an intermediate used for preparing dichroic dyes per the instant invention.

A solution of 1,8-naphthalene diamine (3.5 g, 22 mmol), distilled as in Example 1, acetone (25 ml) and p-toluene sulfonic acid (10 mg) was prepared and stirred at room temperature for 0.5 hour under a nitrogen atmosphere. The mixture was basified with concentrated sodium carbonate (2 ml) and concentrated to about 5 ml volume. The mixture was diluted with ether (150 ml), washed with water and brine, and dried over potassium carbonate. Concentration gave 3.35 g (77%) 2,3-dihydro-2,2-dimethyl perimidine as a pale pink solid. Recrystallization from hexane-ether gave crystals: mp 114°-115° C.; NMR (CDCl$_3$) 7.07(m, 4H), 6.33(m, 2H), 4.06(bs, 2H), 1.42(s, 6H); IR (KBr) 3364, 3290, 1618, 1595 cm$^{-1}$.

EXAMPLE 5

This example illustrates the preparation of 2,3-dihydro-1,2,2,3-tetramethyl perimidine (shown in Table 2), an intermediate used for preparing dichroic dyes per the instant invention.

A mixture of 3M sulfuric acid (8.0 ml), 37% formaldehyde solution (4.6 ml) and THF (10 ml) was prepared in 125 ml erlynmeyer flask and was cooled to 0° C. in a methanol-ice bath. A suspension of sodium borohydride (1.55 g, 40 mmol), 2,3-dihydro-2,2-dimethyl perimidine (prepared in Example 4) (1.0 g, 5 mmol, 198) and THF (15 ml) was added in about 1.5 ml portions over 12 minutes. The addition was controlled so that the temperature of the reaction mixture fluctuated between 5° and 10° C. After addition was completed, the mixture was stirred 8 minutes and then quenched with 25% sodium hydroxide solution (10 ml) and water (30 ml). The mixture was extracted with ether (100 ml) and the extracts washed with water and brine, and dried over potassium carbonate. Concentration gave an oil (1.15 g) that was purified by flash chromatography on silica (hexane-THF, 10:1) to give 2,3-dihydro-1,2,2,3-tetramethyl perimidine (0.85 g, 75%): mp 53°-57° C.; NMR (CDCl$_3$) 7.13(m, 4H), 6.46(m, 2H), 2.90(s, 6H), 1.38(s, 6H); IR (neat) 1583, 1615 cm$^{-1}$.

EXAMPLE 6

This example illustrates the preparation of 2,3-dihydro-1,3-dimethyl-2-propyl perimidine (shown in Table 2), an intermediate used for preparing dichroic dyes per the instant invention.

A mixture of N,N'-dimethyl-1,8-naphthalene diamine (prepared in Example 1) (0.93 g, 5 mmol), distilled butyraldehyde (0.43 g, 6 mmol), p-toluene sulfonic acid (5 mg), and tetrahydrofuran (5 ml), was stirred at room temperature for 15 minutes. The mixture was basified with 25% sodium hydroxide (1.0 ml), diluted with water (20 ml) and extracted with ethyl ether (100 ml). The extract was dried over potassium carbonate and concentrated to an oil which was recrystallized from ether-hexane to give crystals of 2,3-dihydro-1,3-dimethyl-2-propyl perimidine: mp 70°-71° C.; NMR (CDCl$_3$) 7.08(m, 4H), 6.29(m, 2H), 4.22(t, 1H), 3.03(s, 6H), 1.4(m, 4H), 0.8(t, 3H); IR (KBr) 1592, 1582 cm$^{-1}$.

EXAMPLE 7

This example illustrates the preparation of 2,3-dihydro-1,3-dimethyl-2-octyl perimidine (shown in Table 2), an intermediate used for preparing dichroic dyes per the instant invention.

A mixture of N,N'-dimethyl-1,8-naphthalene diamine (prepared in Example 1) (5.0 g, 27 mmol), nonyl aldehyde (3.23 g, 30 mmol), p-toluene sulfonic acid (50 mg), and tetrahydrofuran (50 ml) was prepared and stirred at room temperature for 15 minutes. The mixture was basified with 25% sodium hydroxide (1.0 ml), diluted with water (100 ml) and extracted with ether (300 ml). The extract was dried over potassium carbonate, concentrated to an oil and recrystallized from hexane ether (10:1) to give 2,3-dihydro-1,3-dimethyl-2-octyl perimidine: mp 62°-63° C.; NMR (CDCl$_3$) 7.1(m, 4H), 6.3(m, 2H), 4.25(t, 1H), 3.02(s, 6H), 1.6-1.10(m, 14H), 0.85(t, 3H); IR (KBr) 1598 cm$^{-1}$.

EXAMPLE 8

This example illustrates the preparation of 2,3-dihydro-1,3-dimethyl-2-dodecyl perimidine (shown in Table 2), an intermediate used for preparing dichroic dyes per the instant invention.

A mixture of N,N'-dimethyl-1,8-naphthalene diamine (prepared in Example 1) (0.50 g, 2.7 mmol, 186), tridecanal (0.56 g, 2.85 mmol, 197), p-toluenesulfonic acid (5 mg), and tetrahydrofuran (5 ml) was prepared and stirred at room temperature for 15 minutes. The mixture was basified with 25% sodium hydroxide (1.0 ml), diluted with water (20 ml) and extracted with ether (100 ml). The extract was dried over potassium carbonate, concentrated to give 2,3-dihydro-1,3-dimethyl-2-dodecyl perimidine as a solid: mp 30°-32° C.; NMR (CDCl$_3$) 7.13(m, 4H), 6.32(d, 2H), 4.27(t, 1H), 3.02(s, 6H), 1.7-1.1(m, 22H), 0.85(t, 3H); IR (neat) 1595 cm$^{-1}$.

EXAMPLE 9

This example illustrates the preparation of 2,3-dihydro-1,3-dibutyl-2-octyl perimidine (shown in Table 2), an intermediate used for preparing dichroic dyes per the instant invention.

A mixture of N,N'-dibutyl-1,8-naphthalene diamine (prepared in Example 2) (1.35 g, 5 mmol), nonyl aldehyde (0.78 g, 5.5 mmol), p-toluene sulfonic acid (5 mg) and ethyl acetate (5 ml) was prepared and stirred at room temperature for 15 minutes. More nonyl aldehyde (0.16 g, 1.1 mmol) was added to complete the reaction. The mixture was diluted with ether (50 ml), washed with saturated sodium carbonate (10 ml), washed with water and brine, and dried over potassium carbonate. The extract was concentrated to an oil that would not crystallize from ethyl acetate-hexane. The oil was dried under vacuumn to give crude 2,3-dihydro-1,3-dibutyl-2-octyl perimidine: NMR (CDCl₃) 7.05(m, 4H), 6.35(d, 2H), 4.10(t, 1H), 3.5 and 3.0(m, 4H), 1.8-1.0(m, 20H), 0.9(t, 9H).

EXAMPLE 10

This example illustrates the preparation of 2,3-dihydro-1,2,3-trioctyl perimidine (shown in Table 2), an intermediate used for preparing dichroic dyes per the instant invention.

Nonyl aldehyde was condensed with N,N'-dioctyl-1,8-naphthalene diamine (prepared in Example 3) as described in Example 9. An oil was obtained: NMR (CDCl₃) 7.0(m, 4H), 6.32(d, 2H), 4.07(t, 1H), 3.5 and 3.0(m, 4H), 1.8-1.0(m, 36H), 0.9(t, 9H): IR (neat) 1595 cm⁻¹.

TABLE 2

2,3-Dihydro-1,3-Dialkyl Perimidines

| Example No. | $R_3$ | $R_4$ | $R_5$ | Melting Point (°C.) |
|---|---|---|---|---|
| 4 | H | CH₃ | CH₃ | 114-115 |
| 5 | CH₃ | CH₃ | CH₃ | 53-57 |
| 6 | CH₃ | H | C₃H₇ | 70-71 |
| 7 | CH₃ | H | C₈H₁₇ | 62-63 |
| 8 | CH₃ | H | C₁₂H₂₅ | 30-32 |
| 9 | C₄H₉ | H | C₈H₁₇ | oil |
| 10 | C₈H₁₇ | H | C₈H₁₇ | oil |

EXAMPLE 11

This example illustrates the preparation of the diazo perimidine dye having the structure shown in Table 3. The monoazo nitro amine was prepared as follows. 4-Nitroaniline (16.5 g, 0.12 mol) was dissolved in 10N hydrochloric acid (40 ml) at 75° C. The solution was diluted with water (40 ml), poured over 100 g ice, and cooled to 0° C. Sodium nitrite solution (64.0 ml, 2M) was added over 5 minutes. Within 30 minutes the solution turned almost clear. Urea (1.0 g) was added and stirring was continued at 0° C. for 20 minutes. In a separate beaker distilled m-toluidine (17.1 g, 0.16 mol) was mixed with 5N hydrochloric acid (40 ml) for 5 minutes at room temperature and then cooled to 0°-5° C. The diazonium salt solution was added all at once to the m-toluidine hydrochloride suspension at 0°-5° C. The mixture immediately set up into a thick red paste. The reaction was allowed to proceed for 23 hours at 5° C. The mixture was basified by pouring into saturated potassium carbonate and the resulting solid was washed twice with warm water. Recrystallization of the solid twice from tetrahydrofuran (90 ml) and ethanol (200 ml) gave the monoazo nitro amine as red needles (8.52 g, 28%): mp 152° C.; NMR (CDCl₃) 2.67(s, 3H), 4.15(bs, 2H), 6.5(s and d, 2H), 7.65(d, 1H), 7.85 and 8.22(2d, 4H); IR (KBr) 3430, 3340, 3220, 1645, 1602, 1520 cm⁻¹.

The monoazo nitroamine (0.51 g, 2 mmol) was mixed well with 5N HCl (1.4 ml) and diluted with water (3.6 ml) in a 25 ml beaker. A solution of 2M sodium nitrite (1.1 ml, 2.2 mmol) was added over 3 minutes; the mixture was stirred 2 minutes; and cooled to 0° C. The mixture was stirred occasionally over 10 minutes at 0° C. In a second 50 ml beaker, a mixture of 2,3-dihydro-1,2,2,3-tetramethyl perimidine (prepared in Example 5) (0.565 g, 2.5 mmol), sodium acetate (0.5 g) and acetic acid (8 ml) were mixed and cooled to 0° C. The diazonium solution was poured into the acetic acid solution, all at once. A black-blue paste formed immediately. The mixture was kept at 0° C. for 0.5 hour and basified with saturated potassium carbonate solution. The solid was filtered, washed with warm water twice, and recrystallized from tetrahydrofuran-ethanol (2:1) to give the dye having the structure shown in Table 3 (0.35 g, 36%): mp 231°-233° C.; NMR (CDCl₃ and 5% d6 DMSO) 8.2(d, 3H), 7.8(m, 6H), 7.3(m, 1H), 6.5(m, 2H), 3.1, 2.98, 2.8(3s, 9H), 1.46(s, 6H); IR (KBr) 1588 cm⁻¹. It was measured to have solubility of less than 0.2 wt % in CS 1018.

EXAMPLE 12

This example illustrates the preparation of the diazo perimidine dye having the structure shown in Table 3.

Coupling of 2,3-dihydro-1,3-dimethyl-2-octyl perimidine (Example 7) with the diazonium ion used in Example 11 gave a crude solid. The solid was purified by column chromatography (silica; hexane-THF, 3:1) and recrystallized from THF-ethanol (2:1) to give the diazo perimidine dye having the structure shown in Table 3 (0.06 g): mp 192° C. This dye was measured to have a solubility of less than 0.2 wt % in CS 1018.

EXAMPLE 13

This example illustrates the formation of the diazo perimidine dye having the structure shown in Table 3.

was prepared as follows. To a suspension of 4-hexyloxyaniline (5.8 g, 30 mmol, 193) in 10N hydrochloric acid (10 ml) and water (30 ml) was added 2M sodium nitrite solution (16 ml, 32 mmol) over 5 minutes at 0°-5° C. The solution was stirred occasionally over 30 minutes at 0°-5° C. In a second beaker 2-methoxy-5-methyl aniline (5.5 g, 40 mmol), sodium acetate (8.4 g, 0.1 mol) and acetic acid (50 ml) were mixed well for 5 minutes and cooled to 0°-5° C. The diazonium solution was added to the acetic acid solution all at once and the mixture stirred over 30 minutes at 0°-5° C. The mixture was basified with 25% sodium hydroxide to a pH of 10, filtered, and the solid was washed with hot water. The solid was dried under vacuum and recrystallized from ethanol to give monoazo amine (6.36 g, 62%): mp 97° C.; NMR (CDCl₃) 7.7 and 6.85(2d, 4H), 7.2 and 6.47(2s, 2H), 4.0(m, 4H), 3.8(s, 3H), 2.57(s, 3H), 1.9-1.2(m, 8H), 0.9(t, 3H); IR (KBr) 3460, 3355, 1615, 1602, 1580 cm⁻¹.

The monoazo amine (0.68 g, 2 mmol) was treated as described in Example 11 and coupled with 2,3-dihydro-1,2,2,3-tetramethyl perimidine (prepared in Example 5) to give the diazo perimidine dye having the structure shown in Table 3 (0.76 g, 66%): mp 160°–162° C.; NMR (CDCl₃) 8.34(d, 1H), 7.8(m, 3H), 7.62(s, 1H), 7.3(m, 2H), 6.85(d, 2H), 6.5(t, 2H), 4.0(m, 5H), 3.03, 2.93, 2.70(3s, 9H), 1.42(m, 14H), 0.9(t, 3H); IR (KBr) 1590 cm⁻¹; solubility=0.4 wt % in CS1018 and 0.74 wt % in ZLI 1982; lambda max (CHCl₃)=564 nm, e=31,135.

EXAMPLE 14

This example illustrates the preparation of diazo perimidine dye having the structure shown in Table 3.

Monoazo amine was prepared by diazotizing and coupling 4-Hexyloxyaniline with 3-methylaniline using the procedures described in Example 13.

2,3-Dihydro-1,3-dimethyl-2-octyl perimidine (prepared in Example 7) (0.68 g, 2.2 mmol) was treated with the diazonium ion derived from the above monoazo amine (0.62 g, 2 mmol) as described in Example 11. The crude gummy solid was purified on silica with hexane-THF (6:1) and recrystallized from THF-ethanol (5:1, 12 ml) to give the diazo perimidine dye having the structure shown in Table 3 (0.12 g, 9.5%): mp 90° C.; and lambda max (CHCl₃)=553 nm, e=28,077. This dye was measured to have a solubility in CS1018 of 1.6 wt %.

TABLE 3

Diazo Perimidine Dyes

| Example No. | R₃ | R₄ | R₅ | R₁ | R₂ | Z |
|---|---|---|---|---|---|---|
| 11 | CH₃ | CH₃ | CH₃ | CH₃ | H | NO₂ |
| 12 | CH₃ | H | C₈H₁₇ | CH₃ | H | NO₂ |
| 13 | CH₃ | CH₃ | CH₃ | CH₃ | H | C₆H₁₃O |
| 14 | CH₃ | H | C₈H₁₇ | CH₃ | H | C₆H₁₃O |

EXAMPLE 15

This example illustrates the preparation of the trisazo perimidine dye having the structural formula shown in Table 4.

The diazo amine was prepared as follows. 2-Methoxy-5-methyl aniline (0.85 g, 6.2 mmol) was treated with the diazonium ion derived from monoazo amine (1.55 g, 5 mmol) described in Example 14 using the procedures of Example 11. The solid product (2.0 g) was purified on silica (hexane-ethyl acetate, 4:1) and recrystallized from THF-ethanol (1:3) to give the diazo amine (0.80 g, 35%): mp 96°–98° C.; NMR (CDCl₃) 7.75(m, 4H), 7.3(s, 1H), 6.85(m, 2H), 6.45(s, 2H), 4.15–3.70(m, 7H), 2.75 and 2.63(s, 6H), 1.8–1.20(m, 8H), 0.9(t, 3H).

The diazo amine (0.735 g, 1.6 mmol) was treated with 5N HCl (1.1 ml), water (2.9 ml) and 2M sodium nitrite (0.9 ml) over 5 minutes at room temperature and cooled to 0° C. The diazonium ion solution was poured into a beaker containing a mixture of 2,3-dihydro-1,2,2,3-tetramethyl perimidine (prepared in Example 5)(0.45 g, 2 mmol), sodium acetate (0.4 g), and acetic acid (6 ml) at 0° C. After 0.5 hour the mixture was basified with saturated potassium carbonate (100 ml) and the gummy solid washed twice with warm water. The solid was recrystallized from THF-ethanol (1:2). The solid was purified on silica (hexane-THF, 2:1) to give the trisazo perimidine dye having the structural formula shown in Table 4 (0.20 g, 20%): mp 179°–180° C.; IR 1588 cm⁻¹; lambda max (CHCl₃)=586 nm, e=38,766. It was measured to have a solubility of 0.88 wt % in ZLI 1982 and 0.4 wt % in CS1018.

EXAMPLE 16

This example illustrates the preparation of the trisazo perimidine dye having the structure shown in Table 4.

The diazo amine from Example 15 (0.50 g, 1.1 mmol) was diazotized in a similar manner and added to a solution of 2,3-dihydro-1,3-dimethyl-2-octyl perimidine (0.42 g, 1.3 mmol), sodium acetate (0.4 g), acetic acid (6 ml) and THF (3 ml). The mixture was worked up as in Example 15 and recrystallized from THF-ethanol (2:3) to give the trisazo perimidine dye having the structure shown in Table 4 (0.50 g, 60%): mp 105° C.; NMR (CDCl₃) 8.3(d, 1H), 7.8–7.0(m, 9H), 6.9(d, 2H), 6.4(m, 2H), 4.34(t, 1H), 4.02(m, 5H), 3.12, 3.01, 2.78(3s, 12H), 1.95–1.2(m, 18H), 0.9(m, 6H); IR (KBr) 1590 cm⁻¹; lambda max (CHCl₃)=600 nm, e=35,293. This dye was measured to have a solubility of 5.26 wt % in ZLI 1982 and 0.4 wt % in CS 1018, and an order parameter=0.73 (1 wt % in ZLI 1982).

TABLE 4

Trisazo Perimidine Dyes

| Example No. | R₄ | R₅ |
|---|---|---|
| 15 | CH₃ | CH₃ |

TABLE 4-continued
Trisazo Perimidine Dyes

| Example No. | R$_4$ | R$_5$ |
| --- | --- | --- |
| 16 | H | C$_8$H$_{17}$ |

EXAMPLE 17

This example illustrates the preparation of the tetraazo bis perimidine dye shown in Table 5.

The diazo diamine was prepared by coupling the monoazo nitro amine from Example 11 with 2-methoxy-5-methyl aniline and reducing the diazo nitro amine to the diazo diamine with sodium hydrogen sulfide. Thus, the monoazo nitro amine from Example 11 (7.68 g, 30 mmol) was worked with 5N hydrochloric acid (21 ml) to form a fine paste. The mixture was diluted with water (54 ml), stirred for 5 minutes and 2M sodium nitrite solution (16.5 ml, 33 mmol) added over 5 minutes at room temperature. The mixture was stirred 5 minutes at room temperature and cooled to 0°-5° C. In a separate beaker 2-methoxy-5-methylaniline (5.7 g, 42 mmol) and sodium acetate (7.5 g, 92 mmol) were mixed with glacial acetic acid (51 ml) and water (9 ml) at room temperature and cooled to 0°-5° C. The diazonium solution was added, the mixture stirred at 0°-5° C. for 1 hour, and the mixture basified with saturated potassium carbonate solution. The resulting solid was washed with warm water, and recrystallized from tetrahydrofuran-ethanol (1:2, 180 ml) to give green crystals of diazo nitro amine (8.66 g, 71%): mp 190° C.; NMR (CDCl$_3$-d$_6$ DMSO) 2.58(s, 3H). 2.78(s, 3H), 3.85(s, 3H), 4.36(s, 2H), 6.5(s, 1H), 7.2(s, 1H), 7.65(m, 3H), 7.88 and 8.3(2d, 4H); IR (KBr) 3470, 3360, 1619, 1518, 1503 cm$^{-1}$.

The diazo nitroamine (1.62 g, 4 mmol) in absolute ethanol (50 ml) was heated to 65° C. under a nitrogen atmosphere in an oil bath. A solution of sodium hydrogen sulfide (0.67 g, 12 mmol) in water (4 ml) was added and the mixture heated for 20 minutes at 65°-70° C. An additional amount of sodium hydrogen sulfide (0.34 g, 6 mmol) in water (2 ml) and 10 ml of ethanol was added and the heating continued for 10 minutes. The solvent was removed under reduced pressure and the residue worked with warm water (250 ml) on a steam bath for 10 minutes. The resulting solid was collected and recrystallized from tetrahydrofuran-ethanol (1:4, 25 ml) to give the above illustrated diazo diamine (1.15 g, 77%): mp 196° C.; NMR (CDCl$_3$ and d$_6$ DMSO, 2:1) 2.56(s, 3H), 2.67(s, 3H), 3.82(s, 3H), 5.15(bs, 2H), 5.42(bs, 2H), 6.6(m, 3H), 7.22(s, 1H), 6.7(m, 5H); IR (KBr) 3480, 3320, 1620, 1601, 1505 cm$^{-1}$.

The diazo diamine (0.75 g, 2 mmol) was mixed with 5N HCl (2.8 ml) and water (3.6 ml) to give a fine suspension. Sodium nitrite (2M, 2.2 ml, 4.4 mmol) was added over 3 minutes at room temperature. The stirring was continued for 2 minutes and the mixture cooled to 0° C. The diazonium solution was added to a mixture of 2,3-dihydro-1,2,2,3-tetramethyl perimidine (prepared in Example 5) (1.27 g, 5.6 mmol), sodium acetate (1.0 g) and acetic acid (8 ml) cooled to 0° C. A thick black suspension formed immediately. The mixture was stirred occasionally for 1 hour at 0° C. The mixture was basified by pouring into saturated potassium carbonate solution. The solid was washed twice with warm water and recrystallized twice from THF-ethanol (40 ml, 1:1) to give the dyes shown in Table 5 (0.60 g, 35%): mp 217° C.; NMR (CDCl$_3$) 8.35(d, 2H), 8.1-7.3(m, 13H), 6.55(m, 4H), 4.04(s, 3H). 3.05-2.70(4s, 18H), 1.5(s, 12H); IR (KBr) 1588 cm$^{-1}$; lambda max (CHCl$_3$)=600 nm, e=65,006. The dye was measured to have a solubility of 8.01 wt % in ZLI 1982 and an order parameter of 0.73 (1.0 wt % in ZLI 1982).

EXAMPLE 18

This example illustrates the preparation of tetraazo bis perimidine dye having the structure shown in Table 5.

The diazo diamine described in Example 17 was diazotized as described in the previous experiment and coupled with 2,3-dihydro-2,2-dimethyl perimidine (prepared in Example 4). The crude product was recrystalized from THF-ethanol (evaporated THF) to give the dye shown in Table 5 (0.40 g, 25%): mp 202°-215° C.; IR (KBr) 3360, 1591 cm$^{-1}$; lambda max (CHCl$_3$)=588 nm, e=41,111. This dye was measured to have a solubility in ZLI 1982 of 0.708 wt %.

EXAMPLE 19

This example illustrates the preparation of tetraazo bis perimidine dye having the structure shown in Table 5.

The diazo diamine described in Example 17 was diazotized and coupled with 2,3-dihydro-1,3-dimethyl-2-propyl perimidine as described in Example 17. Purification on silica (hexane-THF, 3:1) and recrystallization (THF-ethanol, 1:1) gave the dye shown in Table 5 (0.08 g, 4.5%): mp 167° C.; NMR (CDCl$_3$) 8.24(d. 2H), 8.1-7.3(m, 13H), 6.4(m, 4H), 4.4(t, 2H), 4.05(s, 3H), 3.13, 3.0, 2.83, 2.78(4s, 18H), 1.8-1.2(m, 8H), 0.85(m, 6H); lambda max (CHCl$_3$)=614 nm, e=66,751. This dyes was measured to have a solubility in ZLI 1982 of 9.34 wt % and an order parameter (1 wt % in ZLI 1982) of 0.73.

EXAMPLE 20

This example illustrates the preparation of tetraazo bis perimidine dye having the structure shown in Table 5.

The diazo diamine described in Example 17 (0.75 g, 2.0 mmol) was diazotized and coupled with 2,3-dihydro-1,3-dimethyl-2-octyl perimidine (1.74 g, 5.6 mmol) using the procedures described in Example 17. The solid was purified on silica (hexane-THF, 2:1) and recrystallized from THF-ethanol to give the dye shown in Table 5 (0.050 g, 2.5%): mp 120° C.; NMR (CDCl$_3$) 8.3(d, 2H), 8.1-7.3(m, 13H), 6.42(m, 4H), 4.4(t, 2H), 4.04(s, 3H), 3.15, 3.04 2.85, 2.78(4s, 18H), 1.8-1.1(m, 28H), 0.85(t, 6H); IR (KBr) 1590 cm$^{-1}$; lambda max (CHCl$_3$)=612 nm, e=68,882. The dye was measured to have a solubility in ZLI 1982 of 4.96 wt % and an order parameter in 1 wt % ZLI 1982 of 0.763.

EXAMPLE 21

This example illustrates the preparation of the tetraazo bis perimidine dye having the structural formula shown in Table 5.

The diazo diamine described in Example 17 (0.375 g, 1 mmol) was diazotized and coupled with 2,3-dihydro-1,3-dimethyl-2-dodecyl perimidine (prepared in Example 8) (1.0 g, 2.56 mmol) in a mixture of sodium acetate (0.5 g) and acetic acid-THF (1:1, 12 ml). The crude solid was worked with hot THF (50 ml) and filtered. The filtrate was purified on silica (hexane-THF, 2.5:1) to give a solid (0.54 g) and recrystallized from THF-ethanol (1:1, 30 ml) to give the dye shown below (0.50 g, 45%): mp 157° C.; NMR (CDCl$_3$) 8.25(d, 2H), 8.1-7.2(m, 13H), 6.4(m, 4H), 4.35(t, 2H), 4.04(s, 3H), 3.15, 3.02, 2.85, 2.75(4s, 18H), 1.8-1.1(m, 44H), 0.9(m, 6H); IR (KBr) 1590 cm$^{-1}$; lambda max (CHCl$_3$)=612 nm, e=72,166. This dye was measured to have a solubility of 1.76 wt % in ZLI 1982 and 1.21 wt % in ZLI 2452; and order parameters of 0.77 (1 wt % in ZLI 1982) and 0.80 (1 wt % in ZLI 2452).

EXAMPLE 22

This example illustrates the preparation of the tetraazo bis perimidine dye having the structural formula shown in Table 5.

The diazo diamine described in Example 17 (0.56 g, 1.5 mmol) was diazotized and coupled with 2,3-dihydro-1,3-dibutyl-2-octyl perimidine (prepared in Example 9)(1.6 g, 4 mmol, 394) using the procedures described in Example 17. The mixture was basified with saturated potassium carbonate and extracted with ether-THF (1:1). The extract was washed with water, filtered, and concentrated to an oil (2,0.5 g). The oil was purified on silica (hexane-THF, 5:1) to give 6f as a glassy solid (0.10 g, 5%); mp 85° C.; lambda max (CHCl$_3$)=633 nm, e=69,473. This dye was measured to have a solubility in ZLI 2452 of greater than 9.45 wt %.

ketone by-product and the aqueous organic solvent by co-distillation.

2. A process as claimed in claim 1 wherein the strong acid is selected from the group consisting of hydrochloric acid, sulfuric acid and p-toluenesulfonic acid.

3. A process for preparing N,N'-dialkyl-1,8-naphthalene diamine comprising:
    (a) alkylating 2,3-dihydro-2,2-dialkyl perimidine with an alkylating agent in a water miscible organic solvent at room temperature to 80° C. in the presence of water and an inorganic base to form 2,3-dihydro-1,3-dialkyl-2,2-dialkyl perimidine; and
    (b) hydrolyzing the 2,3-dihydro-1,3-dialkyl-2,2-dialkyl perimidine with strong aqueous acid in an aqueous organic solvent and removing a ketone by-product and the aqueous organic solvent by co-distillation.

4. A process as claimed in claim 3 wherein:
    (i) the alkylating agent has the formula R-X wherein R is $C_1$-$C_{10}$ alkyl and X is Br, I, tosylate group or mesylate group;
    (ii) the water miscible organic solvent is a ketone; and
    (iii) the inorganic base is selected from the group consisting of potassium carbonate, sodium carbonate, sodium hydroxide and potassium hydroxide.

5. A process as claimed in claim 3 wherein the strong acid is selected from the group consisting of hydrochloric acid, sulfuric acid and p-toluenesulfonic acid.

6. A process as claimed in claim 4 wherein the strong acid is selected from the group consisting of hydrochloric acid, sulfuric acid and p-toluenesulfonic acid.

7. A process as claimed in claim 3, further comprising condensation of 1,8-naphthalene diamine with a ketone to obtain 2,3-dihydro-2,2-dialkyl perimidine.

8. A process as claimed in claim 7 wherein:
    (i) the alkylating agent has the formula R-X wherein R is $C_1$-$C_{10}$ alkyl and X is Br, I, tosylate group or mesylate group;
    (ii) the water miscible organic solvent is a ketone; and
    (iii) the inorganic base is selected from the group consisting of potassium carbonate, sodium carbonate, sodium hydroxide and potassium hydroxide.

9. A process as claimed in claim 7 wherein the strong acid is selected from the group consisting of hydrochloric acid, sulfuric acid and p-toluenesulfonic acid.

10. A process as claimed in claim 8 wherein the strong acid is selected from the group consisting of hydrochloric acid, sulfuric acid and p-toluenesulfonic acid.

TABLE 5

Tetraazo Perimidine Dyes

| Example No. | R$_3$ | R$_4$ | R$_5$ |
|---|---|---|---|
| 17 | CH$_3$ | CH$_3$ | CH$_3$ |
| 18 | H | CH$_3$ | CH$_3$ |
| 19 | CH$_3$ | H | C$_3$H$_7$ |
| 20 | CH$_3$ | H | C$_8$H$_{17}$ |
| 21 | CH$_3$ | H | C$_{12}$H$_{25}$ |
| 22 | C$_4$H$_9$ | H | C$_8$H$_{17}$ |

While the invention has been described with respect to specific embodiments, it should be understood that they are not intended to be limiting and that many variations and modifications are possible without departing from the scope of this invention.

What is claimed is:

1. A process for preparing N,N'-dialkyl-1,8-naphthalene diamine comprising hydrolyzing of 2,3-dihydro-1,3-dialkyl-2,2-dialkyl perimidine with strong aqueous acid in an aqueous organic solvent and removing a